United States Patent [19]

Lee

[11] Patent Number: 5,171,864
[45] Date of Patent: Dec. 15, 1992

[54] DI-(5-HYDROXY-2(5H)-2-OXO-4-FURYL)-METHYL-ALPHA,OMEGA ALKANE-DIOATES AND N,N-BIS-(5-HYDROXY-2(5H)-2-OXO-4-FURYL)METHYL-ALPHA,OMEGA-DIALKANOIC ACID AMIDES AS ANTI-INFLAMMATORY AGENTS

[75] Inventor: Gary C. M. Lee, Laguna Hills, Calif.

[73] Assignee: Allergan, Inc., Irvine, Calif.

[21] Appl. No.: 752,404

[22] Filed: Aug. 30, 1991

[51] Int. Cl.$^5$ .......................... C07F 9/09; C07F 9/40; C07D 307/60
[52] U.S. Cl. .................................. 549/222; 549/318
[58] Field of Search ...................... 549/218, 318, 222

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,447,445 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |
| 4,874,782 | 10/1989 | Bonjouklian et al. | 514/473 |
| 4,916,241 | 4/1990 | Hayward et al. | 549/313 |
| 4,935,530 | 6/1990 | Lee | 549/214 |
| 4,977,146 | 12/1990 | Biftu et al. | 549/218 |
| 5,013,850 | 5/1991 | Lee | 549/222 |
| 5,037,811 | 8/1991 | Lee | 514/99 |
| 5,043,457 | 8/1991 | Lee | 549/222 |
| 5,045,564 | 9/1991 | Lee | 514/471 |

FOREIGN PATENT DOCUMENTS

| | | |
|---|---|---|
| 133376 | 2/1985 | European Pat. Off. . |
| 209274 | 1/1987 | European Pat. Off. . |
| 295056 | 6/1987 | European Pat. Off. . |
| 350878 | 1/1990 | European Pat. Off. . |

OTHER PUBLICATIONS

Bonjuklian et al., Chemical Abstracts, vol. 106, 156260c, p. 670 (1987).
Reynolds et al., J. Am. Chem. Soc., 110, pp. 5172–5177 (1988).
Tocanne et al., Chemical Abstracts 69 76581k, p. 7146 (1968).
Deems et al., Biochimica et Biophysica Acta, 917 pp. 258–268 (1987).
Scheuer et al., Journal of the American Chemical Society 100:1 p. 307 (Jan. 4, 1978).
Graziano et al., Chemical Abstracts 107, (1987), 236559t.
Roll et al., Org. Chem. 1988, 53 3276–8.
Negishi et al., J. Org. Chem 45, pp. 5223–5225, (1980).
E. D. de Silva et al., "Tetrahedron Letters", 21:1611–1614 (1980).
Nakagawa et al., "Aldose reductase inhibitor from Palaun sponges" Chem. Abstract 106:96126b.
Tanaka et al., The Chemical Society of Japan, Chemistry Letters, pp. 633–636 (1983).
Tanis et al., Tetrahedron Letters, vol. 25, No. 40, pp. 4451–4454 (1984)–Furans In Synthesis 4. Silyl Furans As Butenolide Equivalents.
Graziano et al., "Photosensitized Oxidation Of Furans, Part 12, Solvent Effects In Thermal Rearrangement Of The 2,5-Peroxides Of 2,5-Unsubstituted Furans", CA 107:236559t.
David Nettleton et al., Inflammation Research Association, Fifth International Conference Poster Session, Phospholipase A$_2$ Inhibition By Dihydrofuranones, Sep. 23–27, 1990.

Primary Examiner—C. Warren Ivy
Assistant Examiner—A. A. Owens
Attorney, Agent, or Firm—Gabor L. Szekeres; Martin A. Voet; Robert J. Baran

[57] ABSTRACT

Compounds of the formula

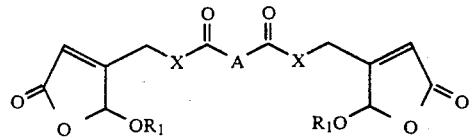

in which R$_1$ independently is H or alkyl of 1 to 20 carbons, CO—R$_2$, CO—O—R$_2$, CO—NH—R$_2$, or PO(OR$_2$)$_2$ or PO(OR$_2$)R$_2$, where R$_2$ independently is H, alkyl of 1 to 20 carbons, phenyl, or lower alkyl substituted phenyl or halogen substituted phenyl; A is (CH$_2$)$_n$ where n ranges between 5 to 30, or A is a a divalent branch chained alkyl radical, or cycloalkyl radical, having a total of 5 to 30 carbons, and X is O or NH, have anti-inflammatory activity.

24 Claims, No Drawings

DI-(5-HYDROXY-2(5H)-2-OXO-4-FURYL)METHYL-ALPHA,OMEGA ALKANE-DIOATES AND N,N-BIS-(5-HYDROXY-2(5H)-2-OXO-4-FURYL)-METHYL-ALPHA,OMEGA-DIALKANOIC ACID AMIDES AS ANTI-INFLAMMATORY AGENTS

BACKGROUND OF THE INVENTION

1. Field of the Invention

The present invention is directed to novel substituted di-[5-hydroxy-2(5H)-4-furanonyl]methyl- alkane-dioates and N,N-bis-[5-hydroxy-2(5H)-4-furanonyl]methyl- dialkanoic acid amides which are active as anti-inflammatory agents. The present invention is also directed to pharmaceutical compositions which comprise one or more of the novel compounds of the invention, to the methods of using these pharmaceutical compositions, and to the chemical processes of making the novel compounds.

2. Brief Description of the Prior Art

Manoalide is a compound isolated from a marine sponge [E. D. de Silva et al., *Tetrahedron Letters* 21:1611-1614 (1980)] which has anti-inflammatory, immunosuppressive and analgesic properties. Manoalide the structure of which is shown below, includes a 5-hydroxy-2(5H)-furanone moiety, attached in the 4-position of the furanone ring to the rest of the molecule. Certain analogs of manolide, such as seco-manoalide and dehydro-seco-manoalide also have anti-inflammatory activity. For further description of the biological activity of manoalide and some of its derivatives reference is made to U.S. Pat. Nos. 4,447,445, 4,786,651, 4,789,749 and to European Patent Application No. 0 133 376 (published on Feb. 20, 1985).

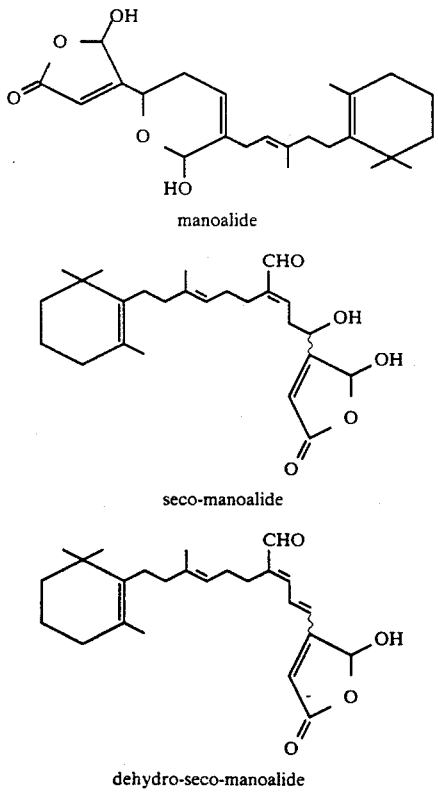

manoalide seco-manoalide dehydro-seco-manoalide

Synthetic analogs of manoalide, particularly analogs having various substituents on the furanone moiety of manoalide, are described in patents and several applications for United States Letters Patent by the same inventor or co-inventor as in the present application, such as U.S. Pat. Nos. 4,935,530 (issued Jun. 19, 1990), 4,957,917 (issued Sep. 18, 1990), 5,013,850 (issued May 7, 1991), 5,037,811 (issued Aug. 6, 1991) and U.S. application Ser. Nos. 699,819 (filed May 13, 1991, pending), 426,243 (filed Oct. 25, 1991, pending), 427,268 (filed Oct. 25, 1989, allowed), 510,364 (filed Apr. 17, 1990, pending), 3,895 (filed Mar. 15, 1990, allowed), 510,367, (filed Apr. 17, 1990, allowed), 693,204 (filed Apr. 30, 1991, pending) and 693,201 (filed Apr. 30, 1991, pending).

Published European Patent Application No. 0 295 056 discloses 4-substituted 5-hydroxy-2(5H)-furanones having anti-inflammatory, immunosuppressive and anti-proliferative activity where the substituents in the 4 position are a variety 1-hydroxyalkyl, 1-acyloxy-alkyl and 1-carbamoyloxy-alkyl groups.

U.S. Pat. No. 4,855,320 discloses 5-arylalkyl-4-alkoxy-2(5H)-furanones as anti-convulsive and anti-epileptic agents.

Published European Patent Application No. 0 209 274 discloses 4-alkyl-5-hydroxy-2(5H)-furanones as anti-inflammatory and anti-allergy agents.

Chemical Abstracts Volume 107 236559t (1987) discloses 4-acyloxy 5-hydroxy-2(5H)-furanones.

SUMMARY OF THE INVENTION

The present invention covers compounds of Formula 1,

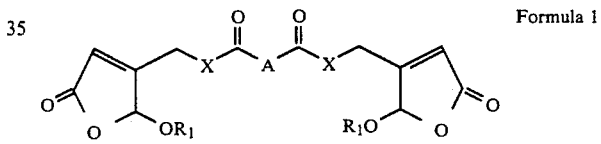

Formula 1 which $R_1$ independently is H or alkyl of 1 to 20 carbons, $CO-R_2$, $CO-O-R_2$, $CO-NH-R_2$, or $PO(OR_2)_2$ or $PO(OR_2)R_2$, where $R_2$ independently is H, alkyl of 1 to 20 carbons, phenyl, or lower alkyl substituted phenyl or halogen substituted phenyl;

A is $(CH_2)_n$ where n ranges between 5 to 30, or A is a divalent branch chained alkyl radical, or cycloalkyl radical, having a total of 5 to 30 carbons, and X is O or NH.

The present invention also covers salts of the above-defined compounds, formed with pharmaceutically acceptable acids or bases, as applicable.

In a second aspect, the present invention relates to pharmaceutical formulations comprising one or more compounds of Formula 1 (or pharmaceutically acceptable salts thereof) in admixture with a pharmaceutically acceptable excipient, for the purpose of treating certain conditions, syndromes or diseases in mammals, including humans. The compounds of the invention have anti-inflammatory, immunosuppressant and anti-proliferative activity. Therefore, the compounds are useful for treating in mammals (including humans) inflammation, rheumatoid arthritis, osteoarthritis, rheumatic carditis, ocular and dermal inflammatory diseases, autoimmune diseases such as allergic bronchial asthma and myasthenia gravis, and for suppressing unwanted immune responses and retarding proliferation of cell.

In still another aspect, the present invention relates to the processes of making the compounds of Formula 1. In general terms, these processes, shown in a summarized fashion in Reaction Scheme 1 comprise the steps of reacting a compound of Formula 2 where X is O or NH, with a suitable derivative of a dicarboxylic acid of the general Formula 3, to provide a compound of general Formula 4, where the CO—A—CO group derived from the dicarboxylic acid links the two (2-trialkylsily-4-furyl)aminomethyl or (2-trailkylsilyl-4-furyl)hydroxymethyl groups with "ester" or amide linkages, depending on the nature of X. The group L in general Formula 3 represents a group suitable for activating the dicarboxylic acid to form ester or amide linkages. Accordingly L can be halogen, chlorine, bromine or iodine or other leaving group. Generally speaking, such reaction conditions are employed for the reaction between the compounds of Formula 2 and Formula 3 which are generally known in the art to effectuate the formation of ester and amide linkages. L may even by OH, and the reaction may be conducted in the presence of dicyclohexyldiimide (DCC) to form the ester or amide linkages.

cover any compounds falling within the respective term as that term is classically used in organic chemistry.

The term "alkyl" as used in the present description and claims includes straight chain alkyl groups, branched chain alkyl groups, cycloalkyl groups, alkyl substituted cycloalkyl groups, and cycloalkyl substituted alkyl groups. Unless the number of carbons is otherwise specified, "lower alkyl" means the former broad definition of "alkyl" groups but with the restriction that the group has 1 to 6 carbon atoms.

Some of the compounds of the invention may contain a chiral center. Other compounds of the invention may contain more than one chiral center. Accordingly, the compounds of the invention may be prepared as mixtures of enantiomeric compounds (where the enatiomers may or may not be present in equal amounts) or as optically pure enantiomers. When there is more than one chiral center, the compounds of the invention may also be prepared as mixtures of diastereomers, or as pure diastereomers, and each diastereomer itself may be a mixture of enantiomers in 1:1, or other, ratios. Alternatively, each diastereomeric compound may be sterically and optically pure. However, all of the above-noted,

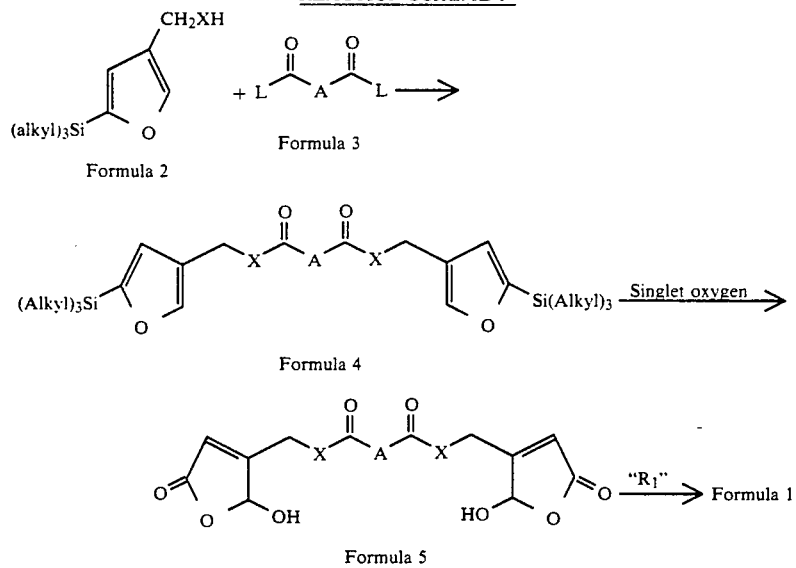

REACTION SCHEME 1

The compounds of Formula 4 are Converted into the compounds of Formula 5 by exposure to singlet oxygen. As is described below in more detail and is specifically illustrated in the appended examples, reaction of the herein-described furane derivatives with singlet oxygen involves irradiation of the furane derivatives of Formula 4 in the presence of oxygen in a suitable solvent. The compounds of Formula 5 are compounds of the invention, where, with reference to Formula 1, $R_1$ is H. The compounds of Formula 1 where $R_1$ is other than hydrogen can be obtained from the compounds of Formula 5 by alkylation, acylation, or other reactions (which per se are well known in the art) to introduce the $R_1$ substituent.

GENERAL EMBODIMENTS

Definitions

The terms "ester", "amine", "amide", "ether" and all other terms and terminology used here, (unless specifically defined in the present description) refer to and forms, including optically pure enantiomers and mixtures thereof, as well as all diastereomers, are within scope of the present invention.

Some of the compounds of the invention may have cis and trans stereoisomers. The scope of the invention includes both pure stereoisomers as well as mixtures thereof.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of the present invention are, with reference to Formula 1 and with respect to the 5-position of the furanone moiety, those where the substituent is hydroxy ($R_1$ is H), acetoxy ($R_1$ is $COCH_3$), 2,2-dimethylpropionyloxy ($R_1$ is $CH_3-C(CH_3)_2-CO$) or where $R_1$ is $CONHR_2$ and $R_2$ is lower alkyl or phenyl, more preferably phenyl.

With reference to the length of the alkyl chain (A) of the dicarboxylic acid residue (CO—A—CO) which connects the two (5-hydroxy-2(5H)-furano-yl)methanol or the two (5-hydroxy-2(5H)-furano-yl)methylamin moieties of the compounds of the present invention, the alkyl chain may contain between approximately 5 to 30 carbons; preferably A is a straight chain divalent alkyl radical represented by $(CH_2)_n$ where n is an integer between 5 to 30, more preferably between 6 to 16 carbons.

The most preferred compounds of the invention are listed below with reference to Formula 6:

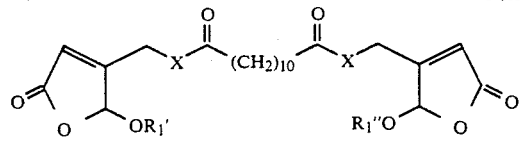

Formula 6

Compound 1 X=O, $R_1'$=H, $R_1''$=H;
Compound 2 X=O, $R_1'$=$CH_3-C(CH_3)_2-CO$, $R_1'$=$CH_3-C(CH_3)_2-CO$;
Compound 3 X=NH, $R_1'$=H, $R_1''$=H;
Compound 4 X=NH, $R_1'$=CONH-phenyl, $R_1'$=CONH-phenyl;
Compound 5 X=NH, $R_1'$=H, $R_1''$=CONH-phenyl.

The compounds of the present invention are useful in pharmaceutical compositions to produce anti-inflammatory, immunosuppressant and anti-proliferative activity. The diseases, syndromes or conditions of mammals (including humans) which can be treated with pharmaceutical compositions containing one or more compounds of the invention (or salts thereof) include: inflammation, rheumatoid arthritis, osteoarthritis, rheumatic carditis, ocular and dermal inflammatory diseases, autoimmune diseases such as allergic diseases, bronchial asthma and myasthenia gravis, unwanted immune responses and unwanted proliferation of cells, psoriasis, acne, atopic diseases and allergic conjunctivitis.

The activity of the compounds of this invention is demonstrated by inhibition of the enzyme phospholipase $A_2$ in vitro and by reduction of inflammation in the mouse ear anti-inflammatory assay in vivo.

Activity of compounds of this invention may also be demonstrated by inhibition of phosphoinositide-specific phospholipase C. This activity has been reported for manoalide may indicate anti-inflammatory utility. Bennett et al, *Molecular Pharmacology* 32:587-593 (1987).

Activity of the compounds may also be demonstrated by inhibition of ornithine decarboxylase, a rate limiting enzyme in cellular growth, which indicates use in treating psoriasis and neoplasis.

The compounds also modify calcium homeostasis. This activity is shown by effect on intracellular calcium levels in experiments using gastric glands, spleen cells, epithelial cells, $GH_3$ cells etc. Calcium is inhibited from entering through the plasma membrane calcium channels and calcium release from intracellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), diseases of the gastrointestinal tract such as ulcer disease, diarrhea, motility due to secretion of acid or $Cl^-$, diseases of the kidney involving renal handling of fluid and electrolytes (metabolic acidosis, alkalosis), and disease of abnormal growth (neoplasia, psoriasis).

The compounds of this invention have activity which is similar to that of manoalide, that is the compounds appear to be devoid of the endocrine properties of the glucocorticoids while having anti-inflammatory and immunosuppressive properties.

In the methods of this invention, the compounds of the invention are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

Pharmaceutical compositions of this invention comprise compounds of Formula 1, and pharmaceutical carriers suitable for the route of administration. Standard methods for formulating pharmaceutical compositions of this type may be found in *Remington's Pharmaceutical Sciences*, Mack Publishing Company, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05-5% of the active ingredient.

A typical cream formulation may contain the following:

| Ingredient | Parts by Weight |
|---|---|
| Water/glycol mixture (15% or more glycol) | 50-99 |
| Fatty alcohol | 1-20 |
| Non-ionic surfactant | 0-10 |
| Mineral oil | 0-10 |
| Typical pharmaceutical adjuvants | 0-5 |
| Active ingredient | 0.05-5 |

A typical ointment formulation may contain the following:

| Ingredients | Parts by Weight |
| --- | --- |
| White petrolatum | 40-94 |
| Mineral oil | 5-20 |
| Glycol solvent | 1-15 |
| Surfactant | 0-10 |
| Stabilizer | 0-10 |
| Active ingredient | 0.05-5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following

| Ingredients | Percent w/w |
| --- | --- |
| Lactose, spray-dried | 40-99 |
| Magnesium stearate | 1-2 |
| Cornstarch | 10-20 |
| Active ingredient | 0.001-20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The assay procedures by which useful biological activity of the compounds of the invention can be demonstrated, are described below.

Calcium Channel (mobilization) Inhibition Assay

Polymorphonuclear leukocytes (PMNa), gastric glands, $GH_3$ cells, A431 cells, spleen cells, human keratinocytes corneal cells, etc. were loaded with the $Ca^{2+}$ sensitive fluorescent dye, Fura-2. The appropriate cell type was chosen and the potency and efficacy of the anti-inflammatory furanones on calcium mobilization, calcium channel inhibition was quantitated. The methods used for A431 cells listed below are representative of those used for other cells A431 cells were detached using a 5-10 min trypsin-EDTA treatment whereas $GH_3$ cells were treated 2 to 5 min with a 1% pancreatin solution. Cells were immediately washed twice in a 20 mM HEPES buffer (pH 7.4) containing 120 mM NaCl, 6 mM KCl, 1 mM $MgSO_4$, 1 mg/ml glucose and 1 mg/ml pyruvate and 1.4 mM calcium (medium A). Approximately $5 \times 10^6$ cells were suspended in medium A and incubated with 4 uM fura-2-AM for 15 min at 37° C.

After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 340 nm and emission wavelength set at 500 nm. The cell suspension was continually stirred, maintained at 37° C. and equilibrated for approximately 5 min before addition of various agents. $[Ca^{2+}]i$ was calculated using the following formula:

$$[Ca^{2+}]_i = 220 \times \frac{F - F\text{min}}{F\text{max} - F}$$

All fluorescence values were measured relative to a EGTA-quenched signal determined as follows: F was the relative fluorescence measurement of the sample. $F_{max}$ was determined by lysing the cells with digitonin (100 ug/ml) in DMSO. After $F_{max}$ was determined the pH was adjusted to 8, with NaOH and $Ca^{2+}$ chelated with 3 mM EGTA to totally quench the fura-2 signal and obtain $F_{min}$.

When quin-2 - was used, cells were incubated with 10 uM quin-2- at 37° C. for hour, washed and then used.

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears [Van Arman, C. G., Clin Pharmacol Other (1974) 16:900-904].

Inhibition of Phosoholipase $A_2$

The effect of compounds of this invention on bee venom phospholipase $A_2$ is determined by the following procedure:
  a. Bee venom phospholipase $A_2$ in 10 uM HEPES (pH 7.4) with 1 mM $CaCl_2$ is incubated with vehicle or test agent for 1.0 hour at 41°.
  b. 1.36 mM phosphotidylcholine, 2.76 mM Triton X-100 are dispersed in buffer by sonication and then mixed with L-3 phosphotidylcholine, 1-palmitoyl-2-(1-$^{14}$C) palmitoyl for 10 min.
  c. Start the reaction by the addition of enzyme (0.495 units/ml).
  d. Incubation for 15 sec. at 41°.
  e. Reaction is terminated by addition of 2.5 ml of isopropanol: n-heptane: 0.5 M $H_2SO_4$ (40:10:1; v:v:v:).
  f. 2.0 ml n-heptane and 1.0 ml $H_2O$ added; mixture centrifuged.
  g. 2.0 ml n-heptane removed and treated with 200-300 mg of silica gel HR60.
  h. Samples centrifuged; 1 ml of n-heptane SN removed and added to 10 ml scintillation fluid.
  i. Samples counted on a scintillation counter.

Inhibition of Phosphoinositide-specific Phospholipase C

The effect of compounds of this invention on phosphoinositide-specific phospholipase C may be determined by procedures described by Bennett et al, Molecular Pharmacology 32:587-593 (1987).

Activity Data

In the above-described phospholipase $A_2$ (PLA$_2$) and phosphoinositide-specific phospholipase C (PLC) assays the compounds of the invention were found to provide 50% inhibition (IC$_{50}$) of the respective venom phospholipase enzymes at the following concentrations (in micromoles), as indicated in Table 1.

TABLE 1

| Compound name or number | PLA$_2$ IC$_{50}$ (um) | PLC IC$_{50}$ (um) |
| --- | --- | --- |
| 1 | 0.07 | >100 |
| 2 | >1.0 | >100 |
| 3 | 0.03 | >100 |
| 4 | >1 | >100 |
| 5 | >1 | >100 |
| manoalide* | 0.03 | 3 |

*Data for monoalide are provided for comparison.

Specific Embodiments

The compounds of the present invention can be made by the synthetic chemical pathways which were described above in general terms, and specifically illustrated in the specific examples below. The synthetic chemist will readily appreciate that the conditions described here in general terms, and specifically, can be generalized to any and all compounds represented by Formula 1. Furthermore, the synthetic chemist will readily appreciate that the herein described synthetic steps may be varied or adjusted by those skilled in the art without departing from the scope and spirit of the invention.

The key starting compounds for the synthesis of the compounds of the present invention are 2-trialkylsilyl-4-hydroxymethylfurans (in Formula 2 X=O) preferably 2- triethylsilyl-4-hydroxymethylfuran (Compound 6), or 2-trimethylsilyl-4-hydroxymethylfuran (Compound 7), and 2-trialkylsilyl-4-aminomethylfuran (in Formula 2 X=NH), preferably 2-triethylsilyl-4-aminomethylfuran (Compound 8), or 2-trimethylsilyl-4-aminomethylfuran (Compound 9). These compounds can be synthesized from commercially available 3-furaldehyde, in the manner described below and also in co-pending application Ser. No. 07/690,444 filed on Apr. 24, 1991, which has been allowed and is expected to issue as a United States patent. The specification of allowed application Ser. No. 07/690,444 is hereby expressly incorporated by reference.

With regard to the reaction step of exposing the intermediate compounds of Formula 4 to the action of singlet oxygen, the following is noted.

The conditions of these reactions are described in detail in connection with the specific examples. In general terms, the reactions are conducted in a mixture of water and acetone or in a mixture of water and tetrahydrofuran, and in some instances in substantially neat tetrahydrofuran, in the presence of an initiator, preferably Rose Bengal dye (preferably polymer bounded), which is added to the reaction mixture. For the synthesis of the compounds of the present invention the reaction is preferably conducted in a mixture of water and tetrahydrofuran. The reaction mixture and vessel is flushed with oxygen and the reaction is conducted at low temperature, at approximately −78° C., or for the herein described reactions preferably at approximately 0° C., under a constant positive pressure of oxygen for a number of hours, typically 1 to 7 hours. The mixture is typically irradiated with a I50 Watt flood lamp. Work-up of the reaction mixture after irradiation usually includes concentration by evaporation of the solvent, followed by chromatography on silica gel, in columns or on preparative silica plates.

The following examples of specific compounds of the invention, and specific examples of the synthetic steps in which the compounds and certain intermediates are made, are set out to illustrate the invention, not to limit its scope.

2-Trimethylsilyl-4-furaldehyde (Compound 10)

n-Butyl lithium (a 2.5M solution in hexane; 28.8 ml, 72 mmol) was added to a solution of morpholine (6.28 ml, 72 mmol) in tetrahydrofuran (700 ml) at −78° under argon. After 20 minutes, 3-furaldehyde (7.0 g, 72 mmol) was added. After another 20 minutes, sec-butyl lithium (a 1.3M solution in cyclohexane; 55.4 ml, 72 mmol) was added dropwise and stirring continued at −78° for 7 hours before trimethylsilyl chloride (27 ml, 216 mmol) was added. Stirring was continued overnight (14 hours) while the cooling bath was allowed to attain room temperature. The solution was poured into ice cold 10% (v/v) hydrochloric acid (200 ml) and after stirring at 0° for 10 minutes, the layers were separated. The aqueous phase was extracted with diethyl ether. All the organic phases were combined, dried (magnesium sulfate) and evaporated to dryness to give a light brown oil, which was purified by flash chromatography on silica using 2% ethyl ether/hexane. Fractions with R$_f$ of about 0.30 (silica, 10% ethyl ether/hexane) on evaporation gave the title aldehyde as a light yellow oil, b.p. 48°–50°/0.25 torr.

$^1$H NMR (CDCl$_3$) 0.29 (s, 9H), 6.98 (s, 1H), 8.25 (s, 1H) and 9.95 (s, 1H).

$^{13}$C NMR (CDCl$_3$) −2.0, 116.2, 128.9, 155.3, 164.1 and 184.5.

HRMS exact mass calculated for C$_8$H$_{12}$O$_2$Si(M+) 168.0607, found 168.0588. See also U.S. Pat. No. 4,935,530, the specification of which is incorporated herein by reference.

2-Triethylsilyl-4-furaldehyde (Compound 11)

n-Butyl lithium (a 2.5M solution in hexane: 30.6 ml, 76.5 mmol) was added to a solution of morpholine (6.66 ml, 76.5 mmol) in tetrahydrofuran (500 ml) at −78° under argon. After 15 minutes, 3-furaldehyde (6.3 ml, 72.8 mmol) was added. After another 20 minutes, sec-butyl lithium (a 1.3M solution in cyclohexane; 59.0 ml, 76.5 mmol) was added dropwise and stirring continued at −78° for about 2 hours before triethylsilylchloride 13.4 ml, 80.1 mmol) was added. Stirring was continued overnight (14 hours) while the cooling bath was allowed to attain room temperature. The solution was poured into ice cold 10% (v/v) hydrochloric acid (100 ml) and another stirring at 0° for 10 minutes, the layers were separated. The aqueous phase was extracted with diethyl ether. All the organic phases were combined, dried (magnesium sulfate) and evaporated down to give an oil, which was distilled under high vacuum to give the 5-treithylsily-3-furaldehyde as a pale yellow oil, boiling point 85°–90°/0.4 torr. p IR (neat) 1680cm$^{-1}$ $^1$H NMR (CDCl$_3$) 0.79 (q, 6H, J=7.3 Hz), 0.90 (t, 9H, J=7.3 Hz), 7.0 (s, 1H), 8.26 (s, 1H) and 9.95 (s, 1H).

$^{13}$C NMR (CDCL$_3$) 2.9, 7.1, 117.2, 128.8, 155.6, 162.3 and 184.6.

HRMS m/e exact mass calculated for C$_{11}$H$_{18}$O$_2$Si(M+) 210.1076, found 210.1071.

4-Hydroxymethyl-2-trimethylsilylfuran (Compound 7)

Trimethylsilyl-4-furaldehyde (Compound 10, 1.57 g, 9.35 mmol) was added to a suspension of sodium borohydride (424 mg, 11.2 mmol) in methanol (10 ml) at 0° C. After 45 minutes, most of the methanol was evaporated and the residue taken up in ethyl ether. The ethyl ether extracts were combined, washed (water), dried (magnesium sulfate) and evaporated to dryness to give an oil, which was purified by flash chromotography on silica using 30% ethyl ether/hexane to give the title alcohol as a pale yellow oil.

H NMR (CDCl$_3$): 7.57 (s, 1H); 6.64 (s, 1H); 4.50 (s, 2H); 2.75 (broad s, 1H); 0.25 (s, 9H).

$^{13}$C NMR (CDCl$_3$): 161.5, 144.0, 125.0, 119.7, 56.2, −1.8.

HRMS exact mass calculated for C$_8$H$_{14}$O$_2$Si: 170.0763, obtained (EI+): 170.0766.

4-Hydroxymethyl-2-triethylsilylfuran (Compound 6)

Sodium borohydride (353 mg, 0.93 mmol) was added portionwise to a solution of 2-triethylsilyl-4-furaldehyde (Compound 11, 1.64 g, 7.79 mmol) in methanol (10 ml) at 0°. After 1 hour, most of the methanol was evaporated and the residue dissolved in a minimum amount of dilute hydrochloric acid. Extraction (ethyl acetate), drying (magnesium sulfate) and evaporation gave an oil, which was purified by flash chromatography on silica using 20% ethyl ether/hexane. Fractions with R$_f$ of about 0.07 (10% ethyl ether/hexane) gave after evaporation the title alcohol as a colorless oil.

$^1$HNMR (CDCl$_3$) 0.76 (q, 6H, J=7.4 Hz), 0.97 (t, 9H, J=7.5 Hz), 1.45 (t, 1H, J=5.3 Hz), 4.56 (d, 2H, J=5.3 Hz), 6.67 (s, 1H) and 7.62 (s, 1H).

HRMS exact mass calculated for C$_{11}$H$_{20}$SiO$_2$(M+) 212.1233 found 212.1231.

(E),(Z)-)-O-Methyl-2-triethylsilyl-4-furaldehyde oxime (Compound 12)

A solution of sodium acetate (1 g, 12.3 mmol) and methoxylamine hydrochloride (1.05 g, 12.3 mmol) in water (5 ml) was added to a solution of 2-triethylsilyl-4-furaldehyde (Compound 11, 860 mg, 4.1 mmol) in ethanol (6 ml) at room temperature. After stirring for 16 hours, most of the ethanol was evaporated and the residue dissolved in water. Extraction (ethyl acetate) and evaporation of the dried (magnesium sulfate) extracts gave an oil, which was purified by flash chromatography on silica using 5% ethyl ether/hexane to give the title oxime as a colorless oil.

$^1$HNMR (CDCl$_3$) 0.79 (q, 6H, J=7.3 Hz), 0.99 (t, 9H, J=7.9 Hz, 3.95 (s, 3H), 4.06 (s, 3H), 6.84 (s, 1H), 7.00 (s, 1H), 7.28 (s, 1H), 7.82 (s, 1H), 8.05 (s, 1H) and 8.34 (s, 1H).

HRMS exact mass calculated for C$_{12}$H$_{21}$NO$_2$Si(M+) 239.1341, found 239.1332.

4-Aminomethyl-2-triethylsilylfuran (Compound 8)

Lithium aluminum hydride (a 1.0M solution in tetrahydrofuran; 0.54 ml, 0.54 mmol) was added dropwise to a solution of (E),(Z)-0-methyl-2-triethylsilyl-4-furaldehyde oxime (Compound 12, 106.2 mg, 0.46 mmol) in tetrahydrofuran (5 ml) at room temperature. After stirring at room temperature overnight (ca. 14 hours), the reaction mixture was quenched with water. Extraction (ethyl ether) and evaporation of the dried (magnesium sulfate) extracts gave an oil, which was purified by flash chromatography on silica using 10% methanol/dichloromethane/1% ammonia. Fractions with R$_f$ of about 0.34 gave after evaporation the title amine as a pale yellow oil.

$^1$H NMR (CDCl$_{13}$) 0.76 (q, 6H, J=7.9 Hz), 0.98 (t, 9H, J=8.4 Hz), 1.87 (br s, 2H), 3.76 (s, 2H), 6.63 (s, 1H) and 7.56 (s, 1H).

HRMS exact mass calculated for C$_{11}$H$_{21}$SiNO(M+) 211.1392, found 211.1389.

Di-(2-triethylsilyl-4-furyl)methyl dodecan-1,12-dioate (Compound 13)

1,12-Dodecanedioyl dichloride (0.44 ml, 1.74 mmol) followed by triethylamine (0.51 ml, 3.65 mmol) was added to a solution of 4-hydroxymethyl-2-triethylsilylfuran (compound 6, 756 mg, 3.57 mmol) in THF (10 ml) at 0 degrees C. After stirring at room temperature overnight, the mixture was diluted with ethyl ether and washed successively with saturated NaHCO$_3$, water and brine. Evaporation of the dried (magnesium sulfate) organic phase gave an oil, which was purified on a silica column using 3% ethyl ether/hexane to give the titled ester.

IR (neat) 1750.

$^1$H NMR (CDCl$_3$) 0.73 (q, 12H, J=7.0 Hz), 0.95 (t, 18H, J=7.0 Hz), 1.22 (br, 12H), 1.60 (m, 4H), 2.28 (t, 4H, J=7.0 Hz), 4.95 (s, 4H), 6.6I (s, 2H) and 7.63 (s, 2H).

$^{13}$CNMR (CDCl$_3$) 2.84, 6.93, 24.7, 28.8, 29.0, 29.1, 34.1, 57.4, 77.4, 120.4, 121.5, 145.9, 159.8 and 174.0

HRMS exact mass calculated for C$_{34}$H$_{62}$NO$_6$Si$_2$ (M+NH$_4$)+ 636.4116, found 636.4109.

Di-[5-hydroxy-2(5H)-2-oxo-4-furyl]methyl dodecan-1,12-dioate (Compound 1)

A mixture of di-(2-triethylsilyl-4-furyl)methyl dodecan-1,12-dioate (Compound 13, 977 mg, 1.58 mmol), Rose Bengal (ca. 3 mg) and water (ca. 1 ml) in THF (I50 ml) was exposed to singlet oxygen at 0 degrees C. for 8 hours. The mixture was filtered and evaporated to dryness to give a solid, which was purified by flash chromatography on silica using 30% ethyl acetate/hexane to give the titled bis-furanone.

IR (CHCl$_3$) 1750.

$^1$HNMR (CDCl$_3$) 1.25 (brs, 12H), 1.55 (brm, 4H), 2.4 (t, 4H, J=7.4 Hz), 4.92 (ddd, 4H, J=16.9 Hz, 1.7 Hz), 6.13 (brs, 4H) and 8.10 (br, 2H)

$^{13}$CNMR (CDCl$_3$) 24.2, 28.3, 28.6, 28.7, 33.1, 38.7, 38.9, 39.2, 39.4, 39.8, 40.1, 40.3, 58.8, 97.7, 117.4, 165.1, 170.3 and 172.8.

HRMS exact mass calculated for C$_{22}$H$_{31}$O$_{10}$ (M+H)+ 455.1917, found 455.1916.

Di-[5tert-butanoyloxy-2(5H)-furano-4yl]methyl dodecan-1,12-dioate (Compound 2)

Ethyl diisopropylamine (52 microliter,, 0.30 mmol), followed by 2,2-dimethylpropionyl chloride (37 microliter, 0.30 mmol) was added to a solution of di-[5-hydroxy-2(5H)-furano-4-yl]methyl dodecan-1,12-dioate (59 mg, 0.13 mmol) in THF (2 ml) at 0 degrees C. under argon. After stirring at 0 degrees C. for 3 hours, the mixture was diluted with ethyl ether and washed successively with water, NaHCO$_3$ solution and brine. Evaporation of the dried (magnesium sulfate) organic layer gave an oil, which was purified by flash chromatography on silica using 20% ethyl acetate/hexane to give the titled diester.

IR (CHCl$_3$) 1800, 1760

$^1$HNMR (CDCl$_3$) 1.21 (s, 18H), 1.23 (br, 12H), 1.60 (m, 4H), 2.35 (t, 4H, J =7.7 Hz), 4.85 (brs, 4H), 6.13 (brs, 2H) and 6.91 (brs, 2H).

$^{13}$CNMR (CDCl$_3$) 24.5, 26.6, 28.8, 28.9, 29.1, 33.6, 38.8, 58.0, 92.6, 119.9, 161.2, 169.1, 173 and 176.6.

HRMS, exact mass calculated for C$_{32}$H$_{50}$NO$_{12}$ (M+NH$_4$)+ 640.3333, found 640.3312.

N,N'-Bis(2-triethylsilyl-4-furyl)methyl-1,12-dodecanoic acid amide (Compound 14)

Diisopropylethylamine (0.46 ml, 2.65 mmol), followed by 1,12-dodecanedioyl dichloride (0.32 ml, 1.26 mmol) was added to a solution of 4-aminomethyl-2-triethylsilylfuran (Compound 8, 533 mg, 2.53 mmol) in dichloromethane at 0 degrees C. under argon. After stirring at room temperature for 8 hours the mixture was quenched with water. Extraction (ethyl ether) and evaporation of the dried (magnesium sulfate) extracts gave an oil which was purified by flash chromatography on silica using 1% methanol/chloroform to give the titled amide.

IR (CHCl$_3$) 1675, 1625, 1510.

$^1$HNMR (CDCl$_3$) 0.75 (q, 12H, J=7.9 Hz), 0.96 (t, 18H, J=7.9 Hz), 1.25 (m, 12H), 1.65 (m, 4H), 2.18 (t, 4H, J=7.8 Hz), 4.24 (d, 4H, J=5.5 Hz), 6.50 (brt, 2H), 6.58 (s, 2H) and 7.53 (s, 2H).

$^{13}$C NMR (CDCl$_3$) 2.72, 6.81, 20.3, 25.4, 28.8, 28.9, 29.0, 29.1, 33.8, 36.2, 45.2, 121.2, 144.2, 159.5 and 173.3.

HRMS exact mass calculated for C$_{34}$H$_{61}$N$_2$O$_4$Si$_2$(M+H)$^+$ 617.4170, found 617.4197.

N,N'-Bis(5-hydroxy-2(5H)-2-oxo-4-furyl)methyl-1,12-dodecanoic acid amide (Compound 3)

A mixture of N,N-bis (2-triethylsilyl-4-furyl)methyl-1,12-dodecanamide (compound 14, 463 mg, 0.75 mmol), Rose Bengal (ca, 3 mg) and water (1 ml) in THF (50 ml) was exposed to singlet oxygen at 0 degrees C. for 5 hours. The mixture was filtered and the filtrate evaporated to dryness to give an oil, which was purified by flash chromatography on silica using 10% methanol/chloroform to give the titled furanone.

IR (CHCl$_3$) 1758, 1661 and 1548.

$^1$H NMR (CD$_3$OD) 1.23 (brs, 12H), 1.62 (brm, 4H), 2.26 (t, 4H, J=7.7 Hz), 4.15 (brs, 4H), 5.89 (brd, 2H, J=1.0 Hz) and 6.09 (brs, 2H)

$^{13}$C NMR (CD$_3$OD) 26.8, 30.2, 30.3, 30.4, 36.8, 37.6, 100.5, 100.6, 118.5, 169.1, 173.1 and 177.0.

HRMS exact mass calculated for C$_{22}$H$_{33}$N$_2$O$_8$ (M+H)$^+$ 453.2236, found 453.2247.

Bis-(2-triethylsilyl-4-furyl)methyl]oxalate (Compound 15)

Oxalyl chloride (0.59 ml, 6.79 mmol) was added dropwise to a solution of 4-hydroxymethyl-2-triethylsilylfuran (compound 6, 1.2 q, 5.66 mmol) and triethylamine (0.95 ml, 6.79 mmol) in dichloromethane (10 ml) at 0 degrees. After 10 minutes, the reaction mixture was quenched with ice. Extraction (dichloromethane) and evaporation of the dried (magnesium sulfate) extracts gave an oil, which was purified by flash chromatography on silica using 5% ethyl ether/hexane. Fractions with R$_f$ of about 0.17 gave, after evaporation, the title oxalate ester as a colorless oil. (83%).

$^1$HNMR (CDCl$_3$) 0.81 (q, 6H, J=7.3 Hz), 1.02 (t, 9H, J=7.3 Hz), 5.24 (s, 2H), 6.73 (s, 1H) and 7.78 (s, 1H).

MS m/e (% abundance) 195(100), 167(16), 115(35) and 87(29).

Singlet oxygen oxidation of bis-[(2-triethylsilyl-4-furyl)methyl]oxalate (Compound 15) in the presence of water, gives the corresponding bis-furanone.

N-(5-Hydroxy-2(5H)2-oxo-4-furyl)methyl-N'-(5-phenylcarbamoyloxy-2(5H) 2-oxo-4-furyl)methyl-1,12-dodecanamide (Compound 4) and N,N'-bis(5-phenylcarbamoyloxy-2(5H)2-oxo-4-furyl)-methyl-1.12-dodeca (Compound 5).

Phenyl isocyanate (29 microliter, 0.27 mmol) was added to a mixture of N,N'-bis(5-hydroxy-2(5H)2-oxo-4-furyl)methyl-1,12-dodecanamide (Compound 3, 116 mg, 0.26 mmol) and copper (I) chloride (27 mg, 0.27 mmol) in DMF (2 ml) at 0 degrees C. under argon. After stirring for 3 hours, the mixture was quenched with water. Extraction (ethyl ether) and evaporation of the dried (magnesium sulfate) extracts gave an oil, which was purified by flash chromatography (10% methanol/chloroform) to give the titled mono-and bis-carbamates Mono-carbamate (Compound 4): R$_f$ (10% methanol/chloroform) 0.21

IR (CHCl$_3$) 3600–3400, 1720 and 1530

$^1$H NMR (CDCl$_3$) 1.27 (m, 12H), 1.60 (m, 4H), 2.25 (t, 4H, J=7.7 Hz), 4.20 (m, 2H), 4.35 (m, 2H), 5.89 (brs, 1H), 6.11 (brs, 2H), 6.99 (s, 1H), 7.05–7.60 (m, 5H) and 7.70 (m, 2H), LRMS (FAB) m/e (% abundance) 594 [(M+Na)$^+$, 20).

Bis-carbamate (Compound 5): R$_f$ (10% methanol/chloroform) 0.37

IR (CHCl$_3$) 3700, 3500–3300, 1805, 1775, 1720, 1680, 1610 and 1540–1520

$^1$HNMR (CDCl$_3$) 1.27 (m, 12H), 1.60 (m, 4H), 2.25 (t, 4H, J=7.9 Hz), 4.20 (dd, 1H, J=17.4 Hz, 4.9 Hz), 4.35 (dd, 1H, J=17.4 Hz, 4.9 Hz), 6.01 (br, 1H), 6.12 (s, 1H), 6.45 (br, 1H), 6.80 (t, 1H), 6.95 (brd, 1H), 6.99 (s, 2H), 7.08 (t, 2H, J=7.6 Hz), 7.20 (t, 4H), 7.35 (m, 4H), 7.50 (brd, 4H), 7.59 (m, 4H), 7.85 (brt, 2H)

LRMS (FAB) m/e (% abundance) 713.8 [(M+Na)$^+$, 50]

What is claimed is:

1. A compound of the formula

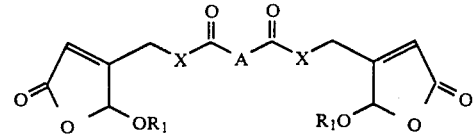

in which R$_1$ independently is H or alkyl of 1 to 20 carbons, CO—R$_2$, CO—O—R$_2$, CO—NH—R$_2$, or PO-(OR$_2$)$_2$ or PO(OR$_2$)R$_2$, where R$_2$ independently is H, alkyl of 1 to 20 carbons, phenyl, or lower alkyl substituted phenyl or halogen substituted phenyl;

A is (CH$_2$)n where n ranges between 5 to 30, or A is a a divalent branch chained alkyl radical, or cycloalkyl radical, having a total of 5 to 30 carbons, and X is O or NH, or a pharmaceutically acceptable salt thereof.

2. A compound of claim 1 where X is O.
3. A compound of claim 2 where A is (CH$_2$)$_n$.
4. A compound of claim 3 where n is an integer between 6 to 16.
5. A compound of claim 2 where R$_1$ is independently selected from a group Consisting of H, CO—R$_2$ and CONHR$_2$.
6. A compound of claim 1 where X is NH.
7. A compound of claim 6 where A is (CH$_2$)$_n$.
8. A compound of claim 7 where n is an integer between 6 to 16.

9. A compound of claim 6 where $R_1$ is independently selected from a group consisting of H, CO—$R_2$ and CONH$R_2$.

10. A pharmaceutical composition for the treatment of a mammal comprising a compound of claim 1 and a pharmaceutically acceptable excipient.

11. A compound of the formula

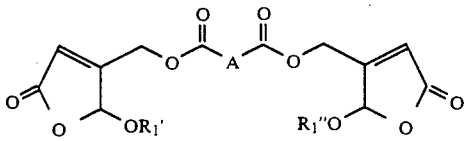

in which $R_1'$ independently is H or alkyl of 1 to 20 carbons, CO—$R_2$, CO—O—$R_2$, CO—NH—$R_2$, where $R_2$ independently is H, alkyl of 1 to 20 carbons, phenyl, or lower alkyl substituted phenyl or halogen substituted phenyl;

$R_1''$ independently is H or alkyl of 1 to 20 carbons, CO—$R_2$, CO—O—$R_2$, CO—NH—$R_2$, where $R_2$ independently is H, alkyl of 1 to 20 carbons, phenyl, or lower alkyl substituted phenyl or halogen substituted phenyl;

A is $(CH_2)_n$ where n ranges between 5 to 30, or A is a a divalent branch chained alkyl radical, or cycloalkyl radical, having a total of 5 to 30 carbons, or a pharmaceutically acceptable salt thereof.

12. A compound of claim 11 where A is $(CH_2)_n$ and n is an integer between 6 to 16.

13. A compound of claim 12 where $R_1'$ and $R_1''$ both are H.

14. The compound of claim 13 where n is 10.

15. A compound of claim 12 where $R_1'$ and $R_1''$ both are $CH_3$—$C(CH_2)_2$—CO.

16. The compound of claim 15 where n is 10.

17. A compound of the formula

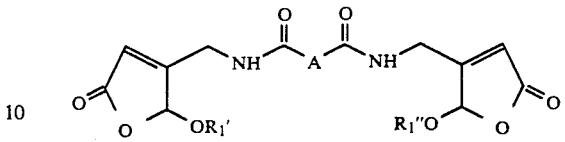

in which $R_1'$ independently is H or alkyl of 1 to 20 carbons, CO—$R_2$, CO—O—$R_2$, CO—NH—$R_2$, where $R_2$ independently is H, alkyl of 1 to 20 carbons, phenyl, or lower alkyl substituted phenyl or halogen substituted phenyl;

$R_1''$ independently is H or alkyl of 1 to 20 carbons, CO—$R_2$, CO—O—$R_2$, CO—NH—$R_2$, where $R_2$ independently is H, alkyl of 1 to 20 carbons, phenyl, or lower alkyl substituted phenyl or halogen substituted phenyl;

A is $(CH_2)_n$ where n ranges between 5 to 30, or A is a a divalent branch chained alkyl radical, or cycloalkyl radical, having a total of 5 to 30 carbons, or a pharmaceutically acceptable salt thereof.

18. A compound of claim 17 where A is $(CH_2)_n$ and n is an integer between 6 to 16.

19. A compound of claim 18 where $R_1'$ and $R_1''$ both are H.

20. The compound of claim 19 where n is 10.

21. A compound of claim 18 where $R_1'$ and $R_1''$ both are CO—NH-phenyl.

22. The compound of claim 21 where n is 10.

23. A compound of claim 18 where $R_1'$ is H, and $R_1''$ is CO—NH—phenyl.

24. The compound of claim 23 where n is 10.

* * * * *

UNITED STATES PATENT AND TRADEMARK OFFICE
CERTIFICATE OF CORRECTION

PATENT NO. : 5,171,864
DATED : December 15, 1992
INVENTOR(S) : Gary C. M. Lee It is certified that error appears in the above-identified patent and that said Letters Patent is hereby corrected as shown below: Title page:

Item (54): line 1, change "(" (first occurrence) to —[— and change ")" (second occurrence) to "]";

In the title, line 4, change "(" (first occurrence) to —[—;

In the title, line 5, change ")" to —]—;

Column 2, line 10, "3,895" should be —493,895—;

Column 2, line 41, before "which" insert —in—;

Column 2, line 66, before "bronchial" insert —diseases,—;

Column 3, line 10, "trailkylsilyl" should be —trialkylsilyl—;

Column 3, line 20, change "by" to —be—;

Column 3, line 48, "Converted" should be —converted—;

Column 4, line 23, after "above-noted" delete the —,—;

Column 5, line 11, "mono" should be — mono- —;

Column 5, line 43, "$R_1$'" should be —$R_1$''—;

Column 6, line 1, after "manoalide" insert —and—;

Column 6, line 10, after "cells" (second occurrence) insert —,—;

Column 6, line 48, after "Company," insert —Easton,—;

Column 8, line 16, after "for" insert —1—;

Column 8, line 27, "_Other_" should be —_Ther_—;

Column 8, line 29, "_Phosoholipase_ should be —_Phospholipase_—;

Column 9, line 61, "I50" should be —150—;

Column 10, line 36, after "hexane" change ":" to —;—;

Column 10, line 54, delete the "p" before the —IR—;

Column 10, line 64, before "Trimethylsilyl" insert — 2- —;

UNITED STATES PATENT AND TRADEMARK OFFICE
CERTIFICATE OF CORRECTION

PATENT NO. : 5,171,864

DATED : December 15, 1992

INVENTOR(S) : Gary C. M. Lee

It is certified that error appears in the above-identified patent and that said Letters Patent is hereby corrected as shown below:

Column 11, line 6, change "H" to —$^1$H—;

Column 11, line 46, after "Hz" insert —)— before the ",";

Column 12, lines 31 & 32, "(I50 ml)" should be —(150 ml)—;

Column 12, line 38, "2.4" should be —2.41—;

Column 12, line 47, "5tert" should be — 5-tert —, and "4yl" should be — 4-yl —;

Column 13, line 47, "Bis-(2-" should be — Bis-[(2- —;

Column 13, line 50, "chIoride" should be —chloride—;

Column 14, line 6, "1.12" should be —1,12—;

Column 14, line 18, after "carbamates" insert —.—;

Column 14, line 63, "Consisting" should be —consisting—;

Column 16, line 2, "$C(CH_2)_2$" should be —$C(CH_3)_2$—.

UNITED STATES PATENT AND TRADEMARK OFFICE
CERTIFICATE OF CORRECTION

PATENT NO. : 5,171,864
DATED : December 15, 1992
INVENTOR(S) : Gary C. M. Lee

It is certified that error appears in the above-identified patent and that said Letters Patent is hereby corrected as shown below:

In the Abstract, line 6 after the structure, delete "a" second occurrence;

Column 14, line 54, Claim 1, delete "a" second occurrence;

Column 15, line 29, delete "a" second occurrence; and

Column 16, line 24, delete "a" second occurrence.

Signed and Sealed this

Thirtieth Day of November, 1993

Attest:

BRUCE LEHMAN

Attesting Officer

Commissioner of Patents and Trademarks